United States Patent [19]

Wilmore

[11] Patent Number: 4,863,901
[45] Date of Patent: Sep. 5, 1989

[54] USE OF GROWTH HORMONE FOR NITROGEN RETENTION UNDER HYPOCALORIC CONDITIONS

[75] Inventor: Douglas W. Wilmore, Brookline, Mass.

[73] Assignee: Brigham & Women's Hospital, Boston, Mass.

[21] Appl. No.: 128,439

[22] PCT Filed: Jan. 9, 1987

[86] PCT No.: PCT/US87/00064
§ 371 Date: Nov. 25, 1987
§ 102(e) Date: Nov. 25, 1987

Related U.S. Application Data

[63] Continuation-in-part of Ser. No. 817,263, Jan. 9, 1986, abandoned.

[51] Int. Cl.[4] .................................... A61K 37/02
[52] U.S. Cl. ............................... 514/12; 514/2; 514/21; 514/561; 514/23; 514/547; 424/600
[58] Field of Search ............... 514/2, 12, 21, 561, 514/547, 23, 777–781; 424/127

[56] References Cited

U.S. PATENT DOCUMENTS

| | | | |
|---|---|---|---|
| 4,009,265 | 2/1977 | Howard | 514/21 |
| 4,283,392 | 8/1981 | Dietze et al. | 514/2 |
| 4,298,601 | 11/1981 | Howard | 514/21 |
| 4,438,144 | 3/1984 | Blackburn | 514/561 |

OTHER PUBLICATIONS

Collipp et al., Metab. 22:589 (1973).
Soroff et al., Ann. Surg. 166:739 (1967).
Beck et al., Metab. 8:699 (1960).
Bergenstal et al., J. Clin. Endo & Metab. 20:1427 (1960).
MRC Panel, The Lancet, 1-3-59, p. 7.
Prudden et al., Surg. Gyn Obs. 102:695 (1956).
Gump et al., Am. J. Med. Sci. 239:27 (1960).
Felig et al., J. Clin. Invest. 50:411 (1971).
Soroff et al., Surg. Gyn. Obs. 111:259 (1960).
Liljedahl et al., Acta Chir. Scand., 122 (1961).
Wilmore et al., Surg. Gyn. Obs., 138:875 (1974).
Roe et al., Surg. Forum 13:369 (1962).
Johnston et al., The Lancet, 16 Mar. 1963, p. 584.
Juergens, Chem. Abstracts, vol. 90:136592k, (1979).
Ward et al., Ann. Europ. Soc. of Enteral and Parenteral Nutrition, Abstract, Book. No. 0.24 (Sep. 1984).

Primary Examiner—Jacqueline M. Stone
Attorney, Agent, or Firm—Saidman, Sterne, Kessler & Goldstein

[57] ABSTRACT

A method and composition for effecting protein accretion in an animal. The composition comprises a hypocaloric dietary component comprising a metabolizable source of nitrogen, carbohydrate, and, optionally, at least one of a triclyeride source, minerals, and vitamins, in conjunction with growth hormone.

The method comprises administering an effective amount of the hypocaloric dietary component and growth hormone, orally or parenterally, to effect a positive nitrogen balance under hypocaloric conditions.

36 Claims, No Drawings

USE OF GROWTH HORMONE FOR NITROGEN RETENTION UNDER HYPOCALORIC CONDITIONS

CROSS REFERENCE TO RELATED APPLICATION

This application is a continuation-in-part of U.S. application Ser. No. 817,263, filed Jan. 9, 1986, now abandoned.

TECHNICAL FIELD

This invention relates to a method and composition for accreting protein in an animal under hypocaloric conditions. The method comprises administering a hypocaloric dietary component to the animal being treated in conjunction with growth hormone. The composition comprises growth hormone and a hypocaloric dietary component. The practice of this invention effects protein buildup in the treated animal where the animal, by design or necessity, is being maintained on a diet comprising from 10 to 95 percent of the resting metabolic requirement (RMR).

BACKGROUND ART

Pituitary growth hormone (GH) is an anabolic protein which promotes growth of tissue and is involved in the regulation of other phases of protein metabolism as well as fat, carbohydrate, and mineral metabolism. Growth hormones from various species differ in their antigenicities, in the range of animals in which they can produce biological responses, in their isoelectric points, N-terminal and C-terminal amino acid residues and amino acid composition. Their molecular weights range from 21,500 for human growth hormone (HGH), to 47,400 for bovine growth hormone. Any growth hormone appears to demonstrate a degree of species-specificity. It is known, however, the humans respond to growth hormone of human or monkey origin.

Growth hormone has been isolated from bovine anterior pituitary, Li, et al., *J. Biol. Chem.* 159, 353 (1945); Wilhelmi et al., *J. Biol. Chem.* 176 735 (1948); Li, U.S. Pat. No. 3,118,815 (1964). Human growth hormone has been isolated from human pituitary, Lewis et al., U.S. Pat. No. 2,974,088 (1961); Reisfeld, et al., *Endocrinology* 71, 559 (1962). Until very recently, isolation of HGH from human cadaver pituitary was the only source for the protein. Accordingly, lack of available material was a primary deterrent for the continuing investigation and definition of therapeutic roles for HGH.

Recently, however, a practical method for synthesizing biologically active growth hormone via recombinant DNA technology has been developed, *The Medical Letter*, vol. 27, 101–102 (1985). Further, recombinant HGH has now been approved by the Food and Drug Administration for use in humans. See, for example, *Genetic Engineering News*, Vol. 5, No. 10, pp 1,8 (1985).

Growth hormone plays a prominent role in protein metabolism and the regulation of growth. This is accomplished by accelerating the rate of transfer of amino acids from the extracellular to the intracellular compartment and incorporating the transferred amino acids into cell proteins. Evidence that growth hormone stimulates the synthesis of messenger RNA, ribosomal RNA, and transfer RNA in liver has led to the hypothesis that growth hormone promotes protein synthesis via gene activation. See *PHYSIOLOGY, Third Edition*, Edited by Selkurt, Little, Brown and Company, page 730 (1971). The overall effect of growth hormone on protein metabolism is evident in the well-documented increase in linear growth resulting from the administration of growth hormone to GH-deficient dwarves, It has been shown that this increase in body cell mass (as reflected by total body potassium) is at the expense of adipose tissue. Collipp, T. J. et al., *Metabolism* 2214, 589–595 (1973).

Similar changes in burn patients treated with growth hormone have been demonstrated as well. Soroff, H. S. et al., *Ann. Surg.* 166, 739–752 (1967). Metabolic studies on normal subjects have consistently shown overall retention of nitrogen and potassium as well as other cellular constituents upon administration of growth hormone. Beck, J. C. et al., *Metabolism* 8, 699–737 (1960); Bergenstall, D. M., et al., *J. Clin. Endo. and Metab.*, 20–11, 1427–1436 (1960); and MRC Panel, *Lancet*, 1, 7–12 (1959). The action of growth hormone in stressed states has been studied extensively in burned patients. Prudden et al. administered bovine growth hormone to four burned patients and demonstrated an anabolic effect dependent on food intake; growth hormone only improved nitrogen balance at high levels of nitrogen intake. Below a certain level of nitrogen intake it appeared to have a deleterious effect, resulting in a worse balance of nitrogen and essential elements. *Surg. Gyn. Obs.*, 102, 695–701 (1956). Burned rats receiving adequate nutrition and growth hormone did not sustain a catabolic response, but when the burned rats were starved, they lost weight at a greater rate than controls. Gump, F. E. et al., *Am. J. Med. Sci.*, 239, 27–32 (1960). Based on this observation, Gump et al. proposed the "critical point" hypothesis which states that "adequate" calories and nitrogen are necessary for growth hormone to exert its anabolic effect. This hypothesis was reinforced by the work of Felig, P. et al., *J. Clin. Invest.*, 50, 411–421 (1971) who administered growth hormone to fasting, obese volunteers and reported reduction in urea excretion which was associated with marked ketoacidosis. This acidosis resulted in increased renal ammonia generation and excretion so that net nitrogen loss was unchanged from previous control periods.

Soroff, H. S. et al., *Surg. Gyn. Obs.*, 111, 259–273 (1960), working with burned patients, was unable to show a beneficial effect from administration of bovine growth hormone. The same authors did show a positive effect in similar study using human growth hormone during the anabolic phase of burn recovery. *Ann. Surg.*, 166, 739–752 (1967). Liljedhal, S. et al., *Acta. Char. Scand.*, 122, 1–14 (1961) and Wilmore, D. W. et al., *Surg. Gyn. Obs.*, 138, 875–884 (1973) demonstrated significant improvement in nitrogen and potassium balance in the post-burn period, the latter specifically with high calorie and protein intake. Moreover, a mood-elevating and appetite stimulating effect was reported which, in the Liljedhal et al. study where ad libitum intake was allowed, led to greater substance intake.

Roe, C. F. et al., *Surg. Forum*, 13, 369–371 (1962), demonstrated an alteration in substrate utilization in postoperative orthopedic patients given growth hormone, with a fall in respiratory quotient (RQ) and a shift to lipid substrates. Johnston, R. D. A. et al., *Lancet*, 584–586 (Mar. 16, 963) showed no improvement in nitrogen balance after herniorrhaphy in patients treated with growth hormone and in matched controls. However, nitrogen intakes were low, caloric provisions were not measured, and only the immediate postoperative period was studied.

Administration of growth hormone to postoperative patients receiving only 5% dextrose has been described by Ward, H. C. et al., in an abstract presented at the Annual European Society of Enteral and Parenteral Nutrition, Abstract Book No. 0.24 (September 1984). The individuals studied excreted less nitrogen and had lower respiratory quotients than the placebo-matched controls. Ward et al. investigated the effect of human GH treatments (0.1 mg/kg/day) given in conjunction with hypocaloric (400 kcals as 2 liters of 5% dextrose/day) peripheral intravenous infusion. No amino acid supplement was present in the feedings.

Dietary control of the nitrogen balance has been studied as well. Howard, U.. Pat. No. 4,009,265, disclosed formulations for the treatment of obesity, describing the use of a low calorie (160-600 Kcal.) diet containing 15-75 grams of amino acids per day to prevent nitrogen loss. Howard, U.S. Pat. No. 4,298,601, described a diet for maintaining nitrogen balance and controlling ketosis and water retention. The daily intake comprised at least 15 grams of amino acids, in the proportion required by humans, and from 15-75 grams of carbohydrates, with a total caloric value of 160-600 kcals. Dietz et al., U.S. Pat. No. 4,283,392, disclosed infusions for low-calorie parenteral nutrition containing 10-200 grams of essential and non-essential amino acids and 50-10,000 ug of kinin per liter of infusion solution. This infusion mixture was designed to replace approximately 1,000 calories per day. According to Dietz et al., the presence of kinin provided a definite improvement in the amino acid utilization in the sense of a anabolic effect relating to the build-up of body-produced proteins.

DESCRIPTION OF THE INVENTION

There are many medical situations which require parenteral feedings. In most such situations, anabolism characterized by protein build-up in the body is essential to achieve maximum recovery in the patient. Unfortunately, the dietary requirements associated with an anabolic state (high protein, high calorie intake) demand the infusion of such large quantities of nutrient that the parenteral infusion process necessitates the use of a central venous catheter to accommodate the volume of infusate.

Intravenous administration of calories, nitrogen, and other nutrients in sufficient quantities to achieve tissue synthesis and anabolism is called total parenteral nutrition. The normal calorie requirement for an adult is approximately 2,500 per day. If these were to be provided totally by Dextrose Injection 5%, approximately 16 liters would be required. Each liter contains 50 grams of dextrose, equivalent to 170 calories. However, it is only possible to administer 3 or 4 liters per day without causing fluid overload. To reduce this fluid volume, the concentration of dextrose would have to be increased. By increasing the dextrose to 25 percent, it would be possible to administer five times the calories in 1/5 the volume. Dextrose Injection 25% is hypertonic, however; it cannot be administered in large amounts into a peripheral vein without sclerosing the vein. Total parenteral nutrition is indicated in patients who are unable to ingest food due to carcinoma or extensive burns; patients who refuse to eat, as in the case of depressed geriatrics or young patients suffering from anorexia nervosa; and surgical patients who should not be fed orally. *Remington's Pharmaceutical Sciences,* 16th ed., Mack Publishing Company, Easton, PA., pg. 1496 (1980).

The use of a central venous catheter requires strict protocol and trained personnel to minimize metabolic septic complications and optimized patient benefits. Further, in many cases, even under the best circumstances, a central vein parenteral nutrition results in increased body fat and water retention but decreased body protein.

Additionally, body protein is essential for normal function and tissue repair. Accordingly, treatment of obesity by dietary restrictions resulting in decreases in body protein, especially where dietary restrictions are imposed for long periods of time, are undesirable. Under the present invention, the subjects would eat small quantities of energy but utilize the body fat, in conjunction with the hypocaloric dietary component and growth hormone, to support maintenance or an increase in body protein, primarily skeletal muscle.

The present invention was developed as the result of a recognition of the need for parenteral solutions which would provide protein build-up while still being suitable for peripheral vein or central venous catheter introduction. Further, there has long been a need for a method for treating obese patients which would permit concomitant weight reduction and protein accretion.

The invention comprises a method and composition for maintaining a positive nitrogen balance (protein accretion or build-up) under hypocaloric conditions. It comprises coadministration of growth hormone and a dietary component comprising a metabolizable source of nitrogen and carbohydrate, the total caloric content of which comprises 10 to 95% of the caloric intake determined to be required to maintain an existing nitrogen level, said dietary component and said growth hormone each administered in a amount effective to produce a positive nitrogen balance.

Best Mode of Carrying Out the Invention

By the term "animal" is included all members of the animal kingdom wherein growth hormone plays a role in protein metabolism; particularly, the term encompasses mammals and birds. The invention is especially suited for the treatment of humans, particularly humans requiring parenteral feeding and humans suffering from obesity.

By the term "coadministering," regardless of tense, is intended the administration of the dietary component and the growth hormone in time-sequence relationship such that the period of biological activity of the growth hormone and the dietary component overlap. Thus in the case of parenteral feeding, the growth hormone may be administered along with the dietary component and drip-infused through a peripheral vein. Alternatively, the growth hormone may be injected periodically, for example, once daily by subcutaneous injections, or drip-infused as a separate component during the parenteral feeding. Where the dietary component is administered orally, the growth hormone may also be administered orally or may be administered parenterally, i.e., by subcutaneous injection.

By the term "hypocaloric dietary component" is intended a dietary component comprising, as a minimum requirement, (1) 4-16 grams of a metabolizable source of nitrogen and (2) carbohydrate, the caloric content of said dietary component being between 10 and 95 percent of the RMR caloric intake. Optionally, up to 50% of the carbohydrate calorie content of the dietary component may be replaced by (3) a triglyceride source, such as fat emulsion. Additionally, the hypocaloric dietary component may contain vitamins, minerals, and/or trace elements as a particular case might indicate.

By the term "a metabolizable source of nitrogen" is intended any dietary source of nitrogen from which protein anabolism in the presence of growth hormone will result. Typically, such sources of nitrogen include dietary proteins, essential amino acids, non-essential amino acids, peptides and the alpha-keto analogues of amino acids.

Preferably the metabolizable source of nitrogen is one in which all of the amino acids, both the essential and non-essential ones, are present in the relative proportions required by the animal in question. The amino acid profile essential to man is well known to those skilled in the art, and, for example, is set out in Rose, W. C. et al., *J. Biol. Chem.*, 217, 987 (1955), incorporated by reference herein. A convenient and inexpensive method of producing the required amino acid mixture is disclosed in U.S. Pat. No. 4,009,265 to Howard, incorporated by reference herein. A protein hydrolysate produced by any conventional procedure, such as by subjecting a protein to hydrolysis using an acid or a proteolase as the hydrolytic agent is analyzed to determine its amino acid profile. It is then adjusted to the optimum profile, either by addition of required quantities of the pure amino acids to make up for any deficiencies and/or by passing the hydrolysate through suitable combinations of anionic and cationic exchange resins to eliminate any excesses. Further, where indicated, the amino acid profile may be altered to accommodate the increase in body protein.

Typical dietary sources of natural protein include egg protein, milk, soy beans, peanuts, fish, and plasma protein. The hypocaloric dietary component is produced in a manner such that its daily administration provides between 4 and 24 grams of nitrogen. A preferred range for the metabolizable source of nitrogen is from 7-21 grams of nitrogen per day, with 8-16 grams of nitrogen most preferred.

By the term "carbohydrate" is intended any digestible and/or metabolizable source of carbohydrate. Typical digestible carbonhydrates include monosaccharides, for example glucose, glucoselactone, fructose, or lactose, disaccharides such as sucrose or maltose, or polysaccharide, for example edible starch or dextrin. Where the carbohydrate is to be provided through parenteral feeding, typical sources of carbohydrates include dextrose solutions, fructose solutions, glycerol solutions, and sorbitol solutions. One preferred carbohydrate source is dextrose solutions.

Optionally, the hypocaloric dietary component may also contain a triglyceride component, typically in the form of a fat emulsion. Where present, the triglyceride component replaces a portion, up to 50% in terms of calories, of the carbohydrate component. Typical sources for the triglyceride component include soybean or safflower emulsion and medium chain triglycerides (MCT), the latter commercially available as 8-carbon or 10-carbon triglycerides (*Remington's*, supra, at page 973).

Additionally, and optionally, the hypocaloric dietary component may contain minerals and vitamins as required. The minerals required by humans are sodium, potassium, calcium, magnesium, manganese, iron, copper, zinc, chloride, phosphorous, sulfur, iodine, and other trace elements. The central vitamins are vitamin A, vitamin B12, vitamin C, vitamin D, vitamin E, vitamin K, riboflavin, peridoxin, niacin, inositol, calcium pantothenate, biotin, folic acid, choline, and thiamin hydrochloride. The so-called minimum daily requirements for each of these minerals and vitamins are well known and may be found in any standard work on nutrition, such as, for example, Davidson, S. et al., "Human Nutrition and Dietetics," 4th Edition, published by E. and S. Livingstone, Edinburgh, pages 244 and 255 (1969). The hypocaloric dietary component is formulated to contain less than the calories equivalent to the RMR requirements for the individual to whom or to which it is to be administered. Typically, the hypocaloric dietary component will contain 10-95 percent, preferably 20-90 percent, most preferably 30-80 percent of the RMR requirement based upon total calories.

By the term RMR is intended that calorie equivalent considered to be the maintenance level of caloric consumption for the individual being treated. This figure may be determined from standard height and weight charts, adjusted for age, or may be determined experimentally. A typical experimental determination of energy expenditure is by indirect calorimetry using measurements of respiratory gas exchange. From these measurements energy requirements, i.e., RMR can be determined. Various methods for determining respiratory gas exchange are known, *Assessment of Energy Requirements In Health and Disease*, published by Ross Laboratories, Columbus, Ohio (1980). A typical experimental determination is provided by the Beckman Metabolic Measurement Cart, described therein.

By the term "growth hormone" is intended either natural or recombinant pituitary growth hormone, regardless of the source. The term is limited only in that the material must demonstrate pituitary growth hormone biological activity in the recipient. Therefore, it also applies to physiologically active equivalents, fragments, or portions of the complete growth hormone molecule. Included within the term is naturally occurring growth hormone which has been isolated from cadavers using techniques well known in the art. Typical techniques for isolation of human growth hormone are disclosed by Lewis et al., supra, and Reisfeld et al., supra. Isolation of growth hormone from bovine anterior pituitary is disclosed by Li et al., supra, and Wilhelmi et al., supra. Also included is recombinant growth hormone; preparation of recombinant growth hormone is disclosed by Goeddell, D. V. et al., *Nature* (London), Vol. 281, pp. 544-548 (1979). In one embodiment, the recombinant growth hormone includes an additional methionine at the N-terminus which is not found on the natural molecule. In a different embodiment, the recombinant growth hormone may be the "mature" form, i.e., having the same N-terminus as the natural growth hormone.

In one embodiment of the invention, the hypocaloric dietary component and growth hormone are combined to form a unitary composition. This composition comprises the subcomponents of the hypocaloric dietary component i.e., as a minimum, carbohydrate in a hypocaloric equivalent, and from 4-16 grams of metabolizable nitrogen, optionally further including at least one of triglycerides as a replacement for up to 50% of the carbohydrate calories, vitamins, and minerals, and an amount of growth hormone effective to provide a positive nitrogen balance under hypocaloric conditions.

The specific amount of growth hormone required by each individual will be dependent upon the age, health, and weight of the recipient, kind of concurrent treatment, if any, frequency of treatment, and the nature of the effect desired. Generally, daily dosages of growth hormone will be from about 0.05 to 0.2 mg per kg of body weight. Normally, from 0.07 to 0.15 mg per kg per day, in one or more applications per day is effective to obtain the desired result. In an alternative approach, the growth hormone, particularly where formulated in a timed-release form, may be administered less frequently, i.e., every other day or every third day.

The composition may be employed in dosage form such as tablets, capsules, powder packets, or liquid solutions, suspensions or elixirs, for oral administration, or sterile liquid for formulations such as solutions or suspensions for parenteral use. In such compositions, the hypocaloric dietary component and growth hormone will be present in such amount as to provide the recipient with the prescribed per day dosage of each component.

Nitrogen balance may be calculated by determining, per 24 hour period, the total nitrogen ingested, the total nitrogen excreted, and subtracting the latter from the former. Where this number is positive, i.e. "a positive nitrogen balance," protein anabolism is occurring. Where this number is negative, protein catabolism is occurring. Alternative methods for determining nitrogen balance are within the skill of the art.

Where the composition is to be administered orally, the growth hormone component must be enterically coated in order to prevent gastric digestion or decomposition of the growth hormone. As is known in the art, enteric coatings do not permit release of a significant quantity of drug until the dosage form passes into the small intestine. Enteric coating compositions are well known to the art, enteric coatings do not permit release of a significant quantity of drug in the stomach but rapidly and completely release the drug when the dosage form passes into the intestine. Enteric coating compositions are well known to the art and generally may be subdivided into three groups, namely, mixtures of fats and fatty acids, shellac and shellac derivatives, and the cellulose acetate phthalates. This last group of compounds, the cellulose acetate phthalates, are preferred, but any of the enteric coatings known and in common use throughout the pharmaceutical industry are suitable for the practice of the invention.

In one aspect of the invention, the hypocaloric dietary component and growth hormone are introduced by peripheral vein infusion. Accordingly, the composition for peripheral vein infusion comprises the hypocaloric dietary component and growth hormone as a unitary composition. In this form, the composition comprises the hypocaloric dietary component and the growth hormone dissolved and/or suspended in an appropriate pharmaceutical carrier. Any carrier in common use and known to the prior art is suitable for this purpose. Typical carriers include Sterile Water for Injection, Sodium Chloride Injection, Ringers Injection, Dextrose and Sodium Chloride Injection, Lactated Rigners Injection, and the like.

In a different embodiment, the hypocaloric dietary component may be administered by peripheral vein infusion, with the growth hormone administered separately. In this embodiment, the appropriate dosage of growth hormone may be administered parenterally, i.e., subcutaneously, intravenously, intramuscularly, or intraperitoneally. Typically, growth hormone is administered parenterally as a 10 mg subcutaneous injection daily.

The materials for use in the method of the invention are ideally suited for the preparation of a kit. Such a kit may comprise a carrier means being compartmentalized to receive in close confinement one or more container means such as vials, test tubes, and the like, each of set container means comprising one of the separate elements to be used in the method. For example, one or more of said container means may comprise the hypocaloric dietary component, compounded for oral or parenteral administration. A further container means may comprise a daily dose of growth hormone, with this daily dose of growth hormone formulated for oral consumption (i.e., enterically coated) or for parenteral administration.

Having generally described the invention, the same will be further illustrated by means fo specific examples which are presented herewith for purposes of illustration only, and are not intended to be limiting thereof, unless otherwise specified.

EXAMPLES

Example 1

Two normal male volunteers were studied for two seven-day periods separated by two-to-three week intervals. They weighed 76 kg and 78 kg, respectively. During each admission, they received parenteral nutrition by peripheral vein infusion containing 165 grams of dextrose, 75 grams of amino acid (12.1 grams N) and 30 grams of triglyceride (given as 10% Intralipid) daily. This mixture provided 1,133 kcal/day. In one 6-day period the subjects received growth hormone (10 mg daily by subcutaneous injection), and during the other period they received saline injections. Every morning respiratory gases were measured, all urine and stool were collected and analyzed for nitrogen, and blood was drawn daily. At the end of the study period, an oral glucose tolerance test was performed, combined with serial forearm flux studies and respiratory gas exchange measurements. Data collected as a result of this experiment appears in Table I below.

TABLE I

|  | Control | Growth Hormone |
|---|---|---|
| Mean N-bal, g/day | −1.8 | +2.2 |
| 6-day cumulative N-bal, g | −10.7 | +13.2 |
| 6:00 a.m. metabolic rate, kcal/day | 1355 | 1260 |
| Plasma glucose, mg/dl | 94 | 103 |
| Blood urea nitrogen, mg/dl | 16 | 10 |
| Insulin, U/ml | 17 | 34 |
| Growth hormone, U/ml | 1.1 | 18 |

The difference in protein accretion between the control and growth hormone period was approximately 150 grams in 6 days. This occurred while the subjects were negative caloric balance and utilizing body fat as fuel. Glucose tolerance tests demonstrated slight glucose resistance associated with marked hyperinsulinemia during the growth hormone period. A marked protein anabolic effect of growth hormone was observed while the subjects received hypocaloric intravenous feeding.

Example 2

In this example, the subjects were studied for at least two separate periods, each of seven day's duration. The studies were paired with caloric level the same for the two study periods. The subjects received growth hormone or placebo during each of the studies. There were at least two week's interval between studies. The treatments were
1. Caloric feeding, with and without growth hormone.
2. Hypocaloric feeding, with and without growth hormone.
3. Fat-free hypocaloric feeding, with and without growth hormone.

The order of growth hormone administration was determined by sequential randomization.

The subjects were admitted to the Clinical research Center in the afternoon of the first day (day 0) and further familiarized with the study procedures. A normal evening meal was allowed, but no further oral intake permitted thereafter, except water, which was freely available.

Adequate calorie intake consisted of calories equivalent to RMR (obtained from standard height and weight tables) plus 25%, and six gm nitrogen/$m^2$. Half of the non-protein calories were administered as carbohydrate and half as fat emulsion. Hypocaloric intake consisted of 50% of the calorie level as calculated above, equally divided between fat emulsion and carbohydrate, with the same nitrogen intake. Fat-free hypocaloric intake excluded the fat emulsion from the hypocaloric intake; thus only 25% of the energy needs were provided.

Where the study involved adequate calorie-parenteral nutrition, a central line was placed under fluoroscopic visualization via the anticubital route using strict aseptic conditions. During the hypocaloric studies, a peripheral venous line was utilized. Normal saline was passed through these lines until the first bag of nutrient solution was hung at 6:00 a.m. the following morning (day 1).

The parenteral nutrition was started at 6:00 a.m. on day 1 and continued through six 24 hour periods. Peripheral lines were changed every 48 hours and administration set for the central lines at the same frequency. Blood pressure was monitored daily and pulse and temperature 4-hourly. The catheter entry sites were regularly inspected and dressings changed every two days. Parenteral solutions were provided, the same volume for both intake levels (approximtely 3 liters).

The subjects were allowed minimal activity through the day, including reading, watching television, and smoking, if this was their usual habit.

During growth hormone treatment periods, at 8:30 each morning, 10 mg of growth hormone, manufactured by a recombinant DNA methodology, was injected subcutaneously. During control periods, a similar volume of saline was injected. The subjects were blinded from the substance injected.

1. Blood Chemistry

Each morning, immediately before the injection of growth hormone or saline, blood was drawn for serum determinations. The following determinations were made:

Every day: Potassium, sodium, free fatty acids, ketons, blood urea nitrogen, glucose.
Days 1, 4, 7: Total protein and fractions, transaminases, insulin, growth hormone, amino acid profile, glycerol, and phosphate.
Day 4: Magnesium, complete blood count and differential.

Serum growth hormone levels were assayed four hours after the growth hormone injection on days 4 and 7.

2. Substrate Balance

The metabolic day began and ended at 6:00 a.m. Urine and stool were collected and each pooled for each 24-hour period. The following measurements were conducted:

Urine measurements: potassium, total nitrogen, urea, creatinine, ammonia, ketone bodies, and C-peptide.
Stool measurements: potassium, total nitrogen.

3. Metabolic Rate

Each subject's day started at 7:30 a.m. when he was awakened, weighed, and oxygen consumnption and carbon dioxide production measured with the Beckman Metabolic Measurement Cart. Respiratory quotient (RQ) ad RMR were calculated. The subject's exhaled respiratory gases were analyzed by breathing through a mouthpiece and tubing with a noseclip in place.

4. Nitrogen Flux

Nitrogen turnover was measured using $N^{15}$-labeled glycine. A dose of $N^{15}$ glycine of 0.5 mg/kg/24 hours was administered during the last three 24-hour periods of each study, administered every three hours in eight equal doses. Three-hourly urine samples were collected during these periods, with aliquots from the last day analyzed by mass spectroscopy for $N^{15}$ enrichment of urinary urea nitrogen, and turnover calculated.

5. Forearm Substrate Flux

On the morning of the final day (day 7) the parenteral nutrition was discontinued at 6:00 a.m. The allotted bloods were drawn and a final dose of growth hormone administered.

At 11:00 a.m. a retrograde anticubital venous catheter was placed and a further catheter positioned in a vein on the back of the contralateral hand. This hand was warmed on a pad and arterialized-venous blood drawn from it. The basal forearm blood flow was measured using venous occlusion plethysmography (initiating two cuts on the arm; one at the wrist and at the upper arm). Basal levels of venous and arterialized-venous glucose, glycerol, free fatty acids, amino acids, and carbon dioxide were then drawn, and using the blood flow, fluxes calculated.

Sixty minutes later, the metabolic chart was used to measure basal levels of oxygen consumption and carbon dioxide production. A further thirty minutes later, a 100-gram oral does of glucose was provided and the metabolic response to this load assessed by measurement of forearm fluxes (as described above, from blood flow and venous-arterialized-venous differences), and respiratory gas exchanged at 30, 60, 120, and 180 minutes. The results appear in Table II below.

TABLE II

| | THE EFFECTS OF HUMAN GROWTH HORMONE ON NITROGEN BALANCE DURING INTRAVENUS FEEDINGS (MEAN OF DAYS 2-6 OF EACH STUDY PERIOD) | | | | | | |
|---|---|---|---|---|---|---|---|
| | | CONTROL PERIOD | | | HGH PERIOD* | | |
| SUBJECT | BODY WEIGHT (kg) | CALORIES in (kcal/d) | NITROGEN in (g/d) | NITROGEN BALANCE (g/d) | CALORIES in (kcal/d) | NITROGEN in (g/d) | NITROGEN BALANCE (g/d) |
| (Adequate Calories Provided) | | | | | | | |

TABLE II-continued

THE EFFECTS OF HUMAN GROWTH HORMONE ON NITROGEN BALANCE DURING
INTRAVENUS FEEDINGS (MEAN OF DAYS 2-6 OF EACH STUDY PERIOD)

| | | CONTROL PERIOD | | | HGH PERIOD* | |
|---|---|---|---|---|---|---|
| SUBJECT | BODY WEIGHT (kg) | CALORIES in (kcal/d) | NITROGEN in (g/d) | NITROGEN BALANCE (g/d) | CALORIES in (kcal/d) | NITROGEN in (g/d) | NITROGEN BALANCE (g/d) |
| 01 | 76.3 | 2262 | 11.6 | +0.5 | 2262 | 11.6 | +2.0 |
| 02 | 78.2 | 2300 | 12.2 | −0.3 | 2300 | 12.2 | +0.5 |
| (Hypocaloric feeding, 50% of caloric requirements provided) | | | | | | | |
| 01 | 76.3 | 1131 | 11.6 | −2.5 | 1131 | 11.6 | +3.0 |
| 02 | 78.2 | 1150 | 12.6 | −1.8 | 1150 | 12.2 | +2.2 |
| 03 | 71.0 | 1020 | 10.9 | −3.5 | 1020 | 10.7 | −0.7 |
| 04 | 63.4 | 985 | 11.0 | −2.8 | 985 | 10.8 | +2.3 |
| (Fat-free hypocaloric feeding, 30%–40% of caloric requirements provided) | | | | | | | |
| 02 | 78.2 | 810 | 12.2 | −4.4 | 810 | 12.2 | +2.0 |
| 04 | 63.4 | 697 | 11.1 | −2.8 | 697 | 10.6 | +0.5 |

*Given as methionyl-HGH, 10 mg subcutaneously/day × 7 days, in all studies except 01 receiving 50% of caloric intake. These individuals received human GH at the same dose.

As may be seen from Table II, administration of growth hormone results in a positive nitrogen balance, indicating protein accretion, under hypocaloric conditions, even where only 30–40% of the adequate calories are supplied.

Example 3

In this example, seven patients with various medical conditions (see Table III) were studied during two separate periods, each of seven days duration, except for one patient (No. 3) who was tested twice using this protocol. The patients received either growth hormone (10 mg, injected subcutaneously) or placebo in addition to 1.3 to 1.7 g protein/kg and a caloric intake equal to 60–100% of RMR. The order of growth hormone-placebo administration was determined by sequential randomization. Nutrition was administered by peripheral vein infusion, except in one case, where the patient received total oral nutrition (see Table IV).

All urine and stool were collected and pooled for each 24 hour period. These samples were analyzed for nitrogen, potassium and phosphorous. The balance of these elements are reported in Table V. Blood was drawn on days 1, 4, and 7 of each week and analyzed for blood urea nitrogen (BUN), glucose and insulin levels. These data are reported in Table VI.

As can be seen in Table V, six of the seven patients receiving growth hormone experienced a positive nitrogen balance that was larger than that observed during the control period. Five of seven patients experienced a positive potassium balance larger than observed during the control period. In addition, all six of the patients tested for phosphorous experienced a positive phosphorous balance that was larger than during the control period. Taken all together, these data indicate protein accretion for patients receiving growth hormone, even when receiving a hypocaloric diet.

All seven patients showed a lower BUN when administered growth hormone compared to the control period. Blood glucose tended to be higher in patients receiving growth hormone (4 of 7) compared to the control period. In addition, insulin levels were significantly higher for all patients, compared to the control period.

TABLE III

PATIENT DATA

| PATIENT | AGE | SEX | ENTRY WEIGHT (kg) | IDEAL WEIGHT (kg) | DIAGNOSIS |
|---|---|---|---|---|---|
| 1 | 46 | F | 81.5 | 68 | Gastric fistula |
| 2 | 35 | M | 63.6 | 69 | S. Bowel fistula Chrom's disease |
| 3a | 78 | F | 67.9 | 61 | S. Bowel fistula postoperative |
| 3b | 78 | F | 68.7 | 61 | S. Bowel fistula postoperative |
| 4 | 19 | M | 66.2 | 70 | 75% Total body surface burns |
| 5 | 78 | M | 64.2 | 75 | Cardiac cachexia |
| 6 | 23 | F | 62.0 | 65 | Short bowel syndrome |
| 7 | 53 | M | 61.0 | 67 | S. Bowel fistula intestinal obstruction |

TABLE IV

NUTRIENT INTAKE

| PATIENT | CALORIES (Kcal/d) | NITROGEN (g/d) | ROUTE | LEVEL OF FEEDING | GROWTH HORMONE THERAPY |
|---|---|---|---|---|---|
| 1 | 1100 | 16 | IV | hypocaloric | 1st |
| 2 | 1100 | 17 | IV | hypocaloric | 2nd |
| 3a | 1100 | 14 | IV | hypocaloric | 2nd |
| 3b | 1900 | 14 | IV | eucaloric | 1st |

TABLE IV-continued

| | NUTRIENT INTAKE | | | | |
|---|---|---|---|---|---|
| PATIENT | CALORIES (Kcal/d) | NITROGEN (g/d) | ROUTE | LEVEL OF FEEDING | GROWTH HORMONE THERAPY |
| 4 | 3000 | 26 | IV | eucaloric | 2nd |
| 5 | 2400 | 11.5 | oral | eucaloric | 1st |
| 6 | 1100 | 15 | IV | hypocaloric | 1st |
| 7 | 1100 | 12 | IV | hypocaloric | 2nd |

TABLE V

| | NITROGEN, POTASSIUM, PHOSPHOROUS BALANCE DATA | | | | | | | | |
|---|---|---|---|---|---|---|---|---|---|
| | NITROGEN (g/d) | | | POTASSIUM (mEq/d) | | | PHOSPHOROUS (mg/d) | | |
| Patient | Control | GH | Control | Control | GH | Control | Control | GH | Control |
| 1 | — | +5.4 | +5.1 | — | +19 | +23 | — | +150 | +94 |
| 2 | +1.4 | +4.4 | — | +49 | +44 | — | −78 | +105 | — |
| 3a | +2.5 | +4.3 | — | +22 | +56 | — | −88 | +214 | — |
| 3b | — | +6.3 | +4.9 | — | +48 | +32 | — | +351 | +3 |
| 4 | −0.9 | +5.9 | — | +7 | +36 | — | −38 | +291 | — |
| 5 | — | +4.7 | +7.3 | — | −5 | −25 | — | — | — |
| 6 | — | +3.8 | +0.5 | — | +45 | +25 | — | +382 | +13 |
| 7 | −1.1 | +2.5 | — | −3.7 | +23 | — | −146 | +127 | — |

TABLE VI

| | BLOOD CHEMICAL VALUES | | | | | | | | |
|---|---|---|---|---|---|---|---|---|---|
| | BUN (mg/dl) | | | GLUCOSE (mg/dl) | | | INSULIN (ucU/ml) | | |
| Patient | Control | G.H | Control | Control | G.H | Control | Control | G.H | Control |
| 1 | — | 21 | 26 | — | 104 | 91 | — | 110 | 26 |
| 2 | 12 | 10 | — | 124 | 106 | — | 41 | 63 | — |
| 3a | 19 | 16 | — | 105 | 118 | — | 7 | 16 | — |
| 3b | — | 16 | 19 | — | 141 | 107 | — | 36 | 8 |
| 4 | 20 | 13 | — | 99 | 125 | — | 5 | 22 | — |
| 5 | — | 16 | 29 | — | 113 | 118 | — | 55 | 12 |
| 6 | — | 11 | 13 | — | 120 | 116 | — | 35 | 20 |
| 7 | 16 | 11 | — | 111 | 114 | — | 16 | 20 | — |

Having now fully described this invention, it will be apparent to one of ordinary skill in the art that the same may be carried out with minor modifications which do not affect the content or spirit thereof.

I claim:

1. A method for effecting protein accretion in an animal comprising administering to said animal:
   (a) a hypocaloric dietary component comprising (i) a metabolizable source of nitrogen and (ii) carbohydrate; and
   (b) growth hormone;
   said hypocaloric dietary component (a) and growth hormone (b) each administered in an amount effective to produce in said animal a positive nitrogen balance.

2. The method of claim 1 wherein said hypocaloric dietary component further comprises at least one of a triglyceride, vitamins and minerals.

3. The method of claim 1 wherein the metabolizable source of nitrogen is selected from the group consisting of dietary proteins, essential and non-essential amino acids, peptides, and the alpha-keto analogues of amino acids.

4. The method of claim 1 wherein the hypocaloric dietary component provides 10–95% of the RMR calorie intake.

5. The method of claim 4 wherein the hypocaloric dietary component provides 30–90% of the RMR calorie intake.

6. The method of 1 wherein the growth hormone is selected from the group consisting of natural and recombinant growth hormone, and the biologically active fraction thereof 7. The method of claim 6 wherein said growth hormone is human growth hormone.

8. The method of claim 6 wherein said growth hormone is administered in an amount of 0.05 to 0.2 mg per kg of body weight per day.

9. The method of claim 1 wherein said hypocaloric dietary component and said growth hormone are administered as a unitary composition.

10. The method of claim 1 wherein said growth hormone is administered separately.

11. The method of claim 1 wherein said hypocaloric dietary component and said growth hormone are administered parenterally or orally.

12. The method of claim 11 wherein said hypocaloric dietary dietary component and said growth hormone are administered parenterally.

13. The method of claim 11 wherein said hypocaloric dietary component and said growth hormone are administered orally.

14. The method of claim 12 wherein said hypocaloric dietary component and said growth hormone are administered by means of peripheral venous infusion.

15. The method of claim 1 wherein said animal is a human.

16. A composition comprising
   (a) a hypocaloric dietary component comprising (i) a metabolizable source of nitrogen, and (ii) carbohydrate; and
   (b) growth hormone;
   said hypocaloric dietary component (a) and growth hormone (b) each contained in an amount effective to produce a positive nitrogen balance in an animal consuming same.

17. The composition of claim 16 wherein said hypocaloric dietary component further comprises at least one of a triglyceride, vitamins, and minerals.

18. The composition of claim 16 wherein said metabolizable source of nitrogen is selected from the group consisting of dietary proteins, essential and non-essential amino acids, peptides, and the alpha-keto analogues of amino acids.

19. The composition of claim 16 wherein said hypocaloric dietary component provides 10-95% of the RMR calorie intake for an animal consuming same.

20. The composition of claim 19 wherein said hypocaloric dietary component provides 30-60% of the RMR calorie intake.

21. The composition of claim 16 wherein said growth hormone is selected from the group consisting of natural growth hormone and recombinant growth hormone, and the biologically active fraction thereof.

22. The composition of claim 21 wherein said growth hormone is human growth hormone.

23. The composition of claim 21 wherein said growth hormone is contained in an amount sufficient to provide from 0.05 to 0.2 mg per kg of body weight per day for an animal receiving same.

24. The composition of claim 16 as a parenterally injectable solution.

25. The composition of claim 16, in liquid or solid form, for oral consumption.

26. The composition of claim 16 wherein said growth hormone is enterically coated.

27. A kit comprising a carrier means, said carrier means being compartmentalized to receive, in close confinement, a first container means comprising a hypocaloric dietary component and a second container means comprising a growth hormone.

28. A method of parenteral feeding of an animal comprising administering through a peripheral vein a protein accreting composition comprising (a) A hypocaloric dietary component comprising (i) a metabolizable source of nitrogen, and (ii) carbohydrate; and (b) growth hormone;

said hypocaloric dietary component (a) and growth hormone (b) each administered in an amount effective to produce in said animal a positive nitrogen balance.

29. The method of claim 28 wherein said hypocaloric dietary component further comprises at least one of a triglyceride, vitamins, and minerals.

30. The method of claim 28 wherein the metabolizable source of nitrogen is selected from the group consisting of dietary proteins, essential and non-essential amino acids, peptides, and the alpha-keto analogues of amino acids.

31. The method of claim 28 wherein the hypocaloric dietary component provides 25-95% of the RMR calorie intake.

32. The method of claim 31 wherein the hypocaloric dietary component provides 30-60% of the RMR calorie intake.

33. The method of claim 28 wherein the growth hormone is selected from the group consisting of natural and recombinant growth hormone, and the biologically active fraction thereof.

34. The method of claim 33 wherein said growth hormone is human growth hormone.

35. The method of claim 33 wherein said growth hormone is administered in an amount of 0.05 to 0.2 mg per kg of body weight per day.

36. The method of claim 28 wherein said animal is a human.

* * * * *